United States Patent [19]

Suzuki et al.

[11] Patent Number: 5,532,158
[45] Date of Patent: Jul. 2, 1996

[54] INTERLEUKIN-2 RECEPTOR DEFICIENT MAMMALS

[75] Inventors: Haruhiko Suzuki; Tak W. Mak, both of Toronto, Canada

[73] Assignee: Ontario Cancer Institute, Toronto, Canada

[21] Appl. No.: 326,896

[22] Filed: Oct. 21, 1994

[51] Int. Cl.$^6$ .............................. C12N 5/00; C12N 15/00
[52] U.S. Cl. ................... 435/240.2; 435/320.1; 435/172.3; 800/2; 800/DIG. 1; 935/24; 935/70
[58] Field of Search ............................ 435/172.3, 240.2, 435/320.1; 800/2, DIG. 1; 935/24, 70

[56] References Cited

FOREIGN PATENT DOCUMENTS

WO92/22645  12/1992  WIPO .

OTHER PUBLICATIONS

Hatakeyama et al., Interleukin–2 Receptor β Chain Gene: Generation of Three Receptor Forms by Cloned Human α and β Chain cDNA's, *Science*, vol. 244, pp. 551–556, 5 May 1989.

Hatakeyama et al., A Restricted Cytoplasmic Region of IL–2 Receptor β Chain Is Essential for Growth Signal Transduction but Not for Ligand Binding and Internalization, *Cell*, vol. 59, pp. 837–845, Dec. 1989.

Hattori et al., Expression of Murine IL–2 Receptor β–Chain on Thymic and Splenic Lymphocyte Subpopulations as Revealed by the IL–2–Induced Proliferative Response in Human IL–2 Receptor α–Chain Transgenic Mice, *J. of Immunol.*, vol. 144, pp. 3809–3815, No. 10, 1990.

Kono et al., Murine Interleukin 2 Receptor β chain: Dysregulated gene expression in lymphoma line EL–4 caused by a promoter insertion, *Proc. Natl. Acad. Sci USA*, vol. 87, pp. 1806–1810, Mar. 1990.

Kündig et al., Immune Responses in Interleukin–2–Deficient Mice, *Science*, vol. 262, pp. 1059–1061, 12 Nov. 1993.

Minami et al., The IL–2 Receptor Complex Its Structure, Function, and Target Genes, *Annu. Rev. Immunol*, 11:245–67, 1993.

Okino et al., Inhibition of Interleukin–2 Synthesis and Interleukin–2 Receptor α Expression on T Cells by a Cell--Free Factor Derived from a CD4+ Regulatory T Cell Clone, *Clin. Immunol. and Immunopathology*, vol. 68, No. 3, pp. 256–262, Sep. 1993.

Schlorle et al., Development and function of T cells in mice rendered interleukin–2 deficient by gene targeting, *Letter to Nature*, vol. 352, pp. 621–624, Aug. 1991.

Takeuchi et al., Expression and role of interleukin–2 receptor β chain on CD4–CD8+ T cell receptor αβ+cells, *Eur J. Immunol.* 22:2929–2935, 1992.

Tanaka et al., In utero treatment with monoclonal antibody to IL–2 receptor β–chain completely abrogates development of Thy–1+ dendritic epidermal cells, *International Immunology*, vol. 4, No. 4, pp. 487–491, Dec. 1991.

Tanaka et al., A Novel Monoclonal Antibody Against Murine IL–2 Receptor β–ChainCharacterization of Receptor Expression in Normal Lymphoid Cells and EL–4 *Cells, J. of Immunol.*, vol. 147, No. 7, pp. 2222–2228, Oct. 1991.

Taniguchi et al., The IL–2/IL–2 Receptor System: A Current Overview, *Cell*, vol. 73, pp. 5–8, Apr. 1993.

Tentori, et al., Essential role of the Interleukin–2–Interleukin 2 Receptor Pathway in Thymocyte Maturation In Vivo, *J. Exp. Med.*, vol. 168, pp. 1741–1747, Nov. 1988.

Thomas A. Waldmann, The IL–2/IL–2 receptor system: a target for rational immune intervention, *TiPS*, vol. 14, pp. 159–164, May 1993.

Thomas A. Waldmann, The IL–2/IL–2 receptor system: a target for rational immune intervention, *Immunology Today*, vol. 14, No. 6, pp. 264–270, 1993.

*Primary Examiner*—Jasemine C. Chambers
*Attorney, Agent, or Firm*—Nancy A. Oleski

[57] ABSTRACT

A mouse lacking expression of a subunit of the IL-2 receptor in certain cells of the immune system is provided. Also provided are methods of using such mice.

2 Claims, 5 Drawing Sheets days after infection of footpads

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

TGGCCTTGTC CGAAAGGTCA         20

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

CTTGACGAGT TCTTCTGAGG         20

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

CCAGGTCTCT CACTACATTG         20

INTERLEUKIN-2 RECEPTOR DEFICIENT MAMMALS

FIELD OF THE INVENTION

This invention relates to a mammal in which the expression of one or more genes has been suppressed. More specifically, the invention concerns insertion of an exogenous DNA molecule into the genomic DNA of a mammal. The exogenous DNA molecule serves to suppress the expression of an endogenous gene in the mammal.

DESCRIPTION OF RELATED ART

The immune system of mammals is comprised of many specialized cells that act together in a highly complex and orchestrated manner to protect the mammal from invading pathogens, toxins, and other foreign substances.

Cells responsible for the specificity of the immune system are referred to as lymphocytes, which are a class of white blood cells. Two important classes of lymphocytes are T cells and B cells. T cells develop in the thymus, and are responsible for cell mediated immunity. There are many types of specialized T cells, such as for example, helper T cells (which enhance the activity of other types of white blood cells), suppressor T cells (which suppress the activity of other white blood cells), and cytotoxic T cells (which kill cells). B cells develop in the bone marrow and exert their effect by producing and secreting antibodies.

Several different classes of molecules are involved in regulating cells that comprise the immune system. One such group of molecules is known as the cytokines, which are produced in and secreted by various types of immune response cells. The cytokines exert their effects on target cells by binding to receptors located on the surface of the target cells; this binding of a cytokine to its receptor transmits a signal into the cell, which can result in changes in gene expression and/or the activity of that cell.

To date, at least 16 interleukins have been identified and designated as IL-1 to IL-16. One of the interleukins, IL-2, has been shown to have a variety of effects on certain cells of the immune system. For example, IL-2 induces proliferation of antigen-primed T-helper cells, supports long-term growth of antigen-specific T cell clones, and enhances the activity of some natural killer (NK) cells (see, for example, Minami et al., *Ann. Rev. Immunol.*, 11:245–267 [1993]). Due to its effects on T cell proliferation, it has been suggested that altering the activity of IL-2/IL-2R (via agents that inhibit IL-2 synthesis or anti-IL-2R directed therapy) could provide a means of preventing allograft rejection, and could be used for treating certain autoimmune disorders and/or certain neoplastic diseases (see, for example, Waldman, *Trends Pharm. Sci.*, 14:159–164 [1993]; Waldman, *Immunol. Today*, 14:264–270 [1993]).

IL-2 appears to exert its effects on cells by binding to its cell surface receptor. The IL-2 receptor ("IL-2R") is expressed on several types of immune system cells, including at least T cells, B cells, NK cells, monocytes, and dendritic epidermal cells. This receptor is comprised of at least three distinct polypeptide subunits (or "chains") termed IL-2Rα, IL-2Rβ, and IL-2Rγ (Leonard et al., *Nature*, 311: 626–631 [1984]; Nikaido et al., *Nature*, 311: 631–635 [1984]; Cosman et al., *Nature*, 312:768–771 [1984]; Hatakeyama et al., *Science*, 244:551–556 [1989], Takeshita et al., *Science*, 257:379–382 [1992]). IL-2Rβ has a long, intracytoplasmic domain and is believed to be essential for proper signal transduction of this receptor molecule (Hatakeyama et al., *Science*, 244:551–556 [1989]). IL-2Rβ has recently been shown to be a component of the IL-15 receptor (Grabstein et al., *Science*, 264:965–968 [1994]). IL-2Rγ is also a component of both the IL-4 receptor and the IL-7 receptor.

A number of techniques have been employed in an effort to characterize the IL-2/IL-2R complex and its effects on the immune system. For example, Takeuchi et al. (*Eur. J. Immunol.*, 22:2929–2935 [1992]) describe the use of a murine monoclonal antibody to IL-2Rβ to study the effect of blocking the IL-2R/IL-2 interaction in a murine thymocyte subpopulation. Tentori et al. (*J. Exp. Med.*, 168:1741–1747 [1988]) describe injecting a murine monoclonal antibody into pregnant mice to block signaling via the IL-2R. Tanaka et al. (*J. Immunol.*, 147:2222–2228 [1991]) describe a monoclonal antibody against murine IL-2RB. The antibody purportedly abolishes IL-2 binding to IL-2R. Tanaka et al. (*Int'l. Immunol.*, 4:487–491 [1992]) describe the use of a monoclonal antibody to IL-2Rβ used to conduct an in utero analysis of the effect of blocking IL-2Rβ on the development of various T cell subpopulations in mouse fetuses. Okino et al. (*Clin. Immunol. Immunopath.*, 68:256–262 [1993]) describe a factor called AS-9 SF, derived from the supernatant of AS-9 T cells, that purportedly selectively blocks expression of IL-2Rα on T cells which prevents T cell proliferation.

While the above described studies have been helpful in understanding the IL-2/IL-2Rβ complex, more complete information on the significance of this complex in the immune system can be obtained by manipulating the genes encoding IL-2 and/or IL-2R in a mammal.

By either increasing or decreasing the level of expression of gene(s) in vivo, it is possible to gain insight as to the overall role the genes have in the in vivo immune response. To this end, a few transgenic or knockout mammals have been produced. Transgenic mammals are those containing exogenous DNA encoding a polypeptide that may or may not naturally occur in that mammal. Knockout mammals typically are genetically engineered to suppress expression of one or more endogenous (i.e. naturally-occurring) genes.

A transgenic non-human mammal is described in PCT patent application WO 92/22645 (published 23 Dec. 1992). The mammal contains a transgene that is a lymphoid gene such as for example CD1, CD2, p56[lck], IL-2Rβ, or fyn. The transgene is operably linked to a DNA sequence encoding a lethal polypeptide.

Hattori et al. (*J. Immunol.*, 144:3809–3815 [1990] describe a transgenic mouse containing a transgene encoding human IL-2Rα.

Kundig et al. (*Science*, 262:1059–1061 [1993]) and Schorle et al., (*Nature*, 352:621–624 [1993]) both describe a knockout mouse that does not express the gene encoding IL-2.

A knockout mouse lacking expression of a CD3-type gene is described in PCT patent application WO 92/22645 (published 23 Dec. 1992).

In view of the devastating effects that can result from immune disorders, there is a need in the art to provide in vivo systems for screening and evaluating drugs useful in the treatment of these disorders.

Accordingly, it is an objective of this invention to provide a mammal in which one or more genes involved in regulation of the immune system have been suppressed through the use of knockout technology.

It is a further objective of this invention to provide methods for preparing, and to prepare a knockout mammal.

SUMMARY OF THE INVENTION

In one aspect, the invention provides a rodent and its progeny in which expression of a subunit of the IL-2 receptor is suppressed. This gene may be suppressed by insertion into the genome of the rodent a nucleic acid molecule comprising at least a portion of an exon of the IL-2 receptor subunit coding sequence linked to a marker sequence; the marker sequence can be the neomycin resistance gene.

In a preferred embodiment, the IL-2 receptor subunit whose expression is suppressed or decreased is the IL-2 receptor β chain.

In another aspect, the invention provides the embryonic stem cell line D3 containing an IL-2 receptor β chain knockout construct.

In still another aspect, the rodent in which expression of a subunit of the IL-2 receptor is suppressed is a mouse.

In yet one other aspect, the invention provides a method of screening a drug for immunostimulatory effects comprising administering the drug to a rodent in which a subunit of the IL-2 receptor has been suppressed, and assaying the mouse for immunostimulation.

BRIEF DESCRIPTION OF THE DRAWINGS

FIG. 2A shows the response of T cells from 3 week old mice. Gray colored boxes represent the response of T cells from heterozygous knockout mice, and black boxes represent the response of T cells from homozygous knockout mice (2 replicates are shown for homozygous knockout mice).

FIG. 3 depicts the cytotoxic T lymphocyte response of wild-type, heterozygous IL-2Rβ knockout and homozygous IL-2Rβ knockout mice to lymphocytic choriomeningitis virus (LCMV). The response is shown as footpad swelling. FIG. 3A and FIG. 3B are replicates.

FIG. 4 depicts the IgM (blackened characters) and IgG (open characters) antibody levels in homozygous (triangles) and heterozygous (circles) IL-2Rβ knockout mice injected with VSV.

DETAILED DESCRIPTION OF THE INVENTION

Figure 1:
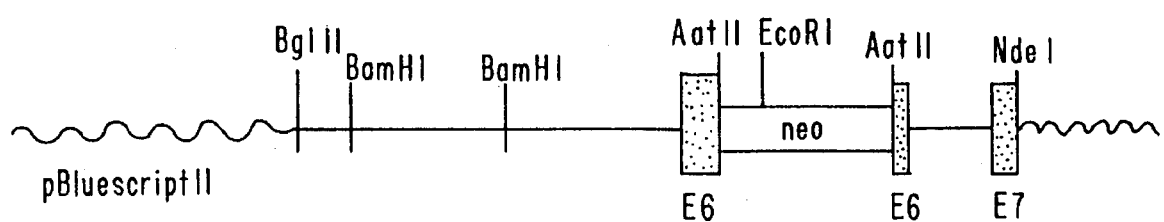
FIG. 1 depicts the knockout construct electroporated into mouse ES cells. Selected restriction endonucleases sites are indicated. The term "neo" refers to the DNA encoding the neomycin phosphotransferase gene. The vector pBluescript-tII is also indicated.

The term "knockout" refers to partial or complete reduction of the expression of at least a portion of a polypeptide encoded by an endogenous gene of a single cell, selected cells, or all of the cells of a mammal.

The term "knockout construct" refers to a nucleotide sequence that is designed to decrease or suppress expression of a polypeptide encoded by an endogenous gene in one or more cells of a mammal. The nucleotide sequence used as the knockout construct is typically comprised of (1) DNA from some portion of the endogenous gene (one or more exon sequences, intron sequences, and/or promoter sequences) to be suppressed and (2) a marker sequence used to detect the presence of the knockout construct in the cell. The knockout construct is inserted into a cell with chromosomal DNA that contains the endogenous gene to be knocked out. The knockout construct can then integrate with the DNA of the cell in such a position so as to prevent or interrupt transcription of the gene to be knocked out. Such insertion usually occurs by homologous recombination (i.e., regions of the knockout construct that are homologous or complimentary to endogenous DNA sequences hybridize to each other when the knockout construct is inserted into the cell; these regions can then recombine so that the knockout construct is incorporated into the corresponding position of the endogenous DNA).

Typically, the knockout construct is inserted into an embryonic stem cell (ES cell) where the cell is an undifferentiated cell, usually derived from an embryo or blastocyst of the same species as the developing embryo into which it is subsequently inserted. The knockout construct can then integrate into the ES cell genomic DNA, usually by the process of homologous recombination. This ES cell can then be integrated with the developing embryo.

The phrases "disruption of the gene" "gene disruption" "suppressing expression", and "gene suppression", refer to insertion of a nucleotide sequence knockout construct into a region of an endogenous gene (usually one or more exons) and/or the promoter region of a gene so as to decrease or prevent expression of that gene in the cell. Insertion is usually accomplished by homologous recombination. By way of example, a nucleotide sequence knockout construct can be prepared by inserting a nucleotide sequence comprising an antibiotic resistance gene into a portion of an isolated nucleotide sequence that is complimentary to the endogenous DNA sequence (promoter and/or coding region) to be disrupted. When this knockout construct is then inserted into a cell, the construct can integrate into the genomic DNA. Thus, many progeny of the cell will no longer express the gene at least in some cells, or will express it at a decreased level, as the endogenous nucleotide sequence of the gene is now disrupted by the antibiotic resistance gene.

The term "marker sequence" refers to a nucleotide sequence that is (1) used as part of a larger nucleotide sequence construct (i.e., the "knockout construct") to disrupt the expression of the gene(s) of interest (such as, for example, IL-2R subunits), and (2) used as a means to identify those cells that have incorporated the knockout construct into the genome. The marker sequence may be any sequence that serves these purposes, although typically it will be a sequence encoding a protein that confers a detectable trait on the cell, such as an antibiotic resistance gene or an assayable enzyme not typically found in the cell. Where the marker sequence encodes a protein, the marker sequence will also typically contain either a homologous or heterologous promoter that regulates its expression.

The terms "rodent" and "rodents" refer to all members of the phylogenetic order Rodentia including any and all progeny of all future generations derived therefrom.

The term "murine" refers to any and all members of the family Muridae, including rats and mice.

The term "progeny" refers to any and all future generations derived or descending from a particular mammal, i.e., a mammal containing one or more knockout constructs inserted into its genomic DNA, whether the mammal is heterozygous or homozygous for the knockout construct. More preferred progeny are those that are homozygous for the knockout construct. Progeny of any successive generation are included herein such that the progeny, the F1, F2, F3, generations and so on indefinitely containing the knockout construct are included in this definition.

The term "immunomodulatory" refers to changes in the level of expression or activity (i.e., a detectable increase or decrease) of any component (i.e., cell, polypeptide, protein, and/or nucleic acid molecule) of the immune system in a mammal as compared to the average expression or activity of that same component for the same mammalian species that has not been genetically altered (i.e., the wild-type). Immunomodulation may be detected by assaying the level of B cells, any type of T cells, antigen presenting cells, and/or any other cells believed to be involved in immune function. Additionally or alternatively, immunomodulation may be detected by evaluating 1) the level of expression of particular genes believed to have a role in the immune system, 2) the level of particular compounds such as cytokines (interleukins and the like) or other molecules that have a role in the immune system such as, for example, receptors for various cytokines, and/or 3) the level of particular enzymes, proteins, and the like that are involved in immune system functioning.

The terms "IL-2 receptor" and "IL-2R" refer to an interleukin-2 receptor that is a naturally occurring multisubunit polypeptide complex expressed on the cell surface of certain mammalian cells. One isoform of IL-2R, the heterotrimer "high affinity" form, comprises the IL-2α (Shimuzu et al., *Nuc. Acid Res.*, 13: 1505–1516 [1985]), IL-2β (Kono et al., *Proc. Natl. Acad. Sci. USA*, 87:1806–1810 [1990]) and IL-2β (Kumaki et al., *Biochem. Biophys. Res. Comm.*, 193:356–363 [1993]) subunits (or chains). For purposes of the present invention, other isoforms of IL-2R such as the "low affinity" heterodimer IL-2β/IL-2γ are included within the scope of this invention. It is to be understood that the nucleotide sequence, and possibly the amino acid sequence as well, of each subunit may naturally vary from species to species; these sequences may also vary within a given species due to naturally occurring allelic variations of the gene encoding each subunit. All such variants are contemplated to be within the scope of this invention.

Knockout Technology

1. Selection Of Knockout Gene(s)

The native or endogenous gene(s) to be knocked out may be any gene provided that at least some sequence information on the DNA to be disrupted is available to use in the preparation of both the knockout construct and the screening probes. Usually, the DNA to be used in the knockout construct will contain at least one or more exon and/or intron regions of the genomic DNA sequence, and/or a promoter region, but a cDNA sequence may be used, provided the cDNA is sufficiently large. Generally, the DNA molecule will be at least about 1 kilobase (kb) in length and preferably 3–4 kb in length, thereby providing sufficient complementary sequence for hybridization to chromosomal DNA when the knockout construct is introduced into the genomic DNA of the ES cell (discussed below). A preferred gene to be knocked out is one encoding a polypeptide that is a subunit of the interleukin-2 receptor molecule. A more preferred gene is one that encodes the α, β or γ chain subunit of the IL-2 receptor. A most preferred gene is one that encodes the IL-2 D chain subunit.

Included within the scope of this invention is a mammal in which two or more genes have been knocked out. Such a mammal can be generated by repeating the procedures set forth herein for generating each knockout mammal, or by breeding two mammals, each with a single gene knocked out, to each other, and screening for those offspring that have the double knockout genotype.

Also included within the scope of this invention is a mammal in which 1) one or more genes have been knocked out, and 2) one or more transgenes have been inserted.

The native genomic or cDNA molecule to be used in preparing the knockout construct can be obtained using methods well known in the art such as those described by Sambrook et al. (*Molecular Cloning: A Laboratory Manual*, Cold Spring Harbor Laboratory Press, Cold Spring Harbor, N.Y. [1989]). Such methods include, for example, PCR amplification of a particular DNA sequence using oligonucleotide primers, or screening a genomic library with a cDNA probe encoding at least a portion of the same gene in order to obtain at least a portion of the genomic sequence. Alternatively, if a cDNA sequence is to be used in a knockout construct, the cDNA may be obtained by screening a cDNA library with oligonucleotide probes or antibodies (where the library is cloned into an expression vector). If a promoter sequence is to be used in the knockout construct, synthetic DNA probes or primers can be designed for screening a genomic library or for amplification using PCR, respectively.

As used herein, "transgene" refers to a DNA molecule encoding a polypeptide, wherein the DNA molecule is operably linked to a promoter. The transgene DNA encoding the polypeptide may be 1) homologous or heterologous to the mammal, 2) the full length sequence or a fragment thereof, and/or 3) a naturally occurring sequence, an analog of a naturally occurring sequence, a synthetic sequence, or a hybrid occurring between one or more naturally occurring sequence(s) and/or synthetic sequence(s).

Where the DNA sequence of the native gene is known, it may be manufactured synthetically, using chemical synthesis methods such as those described by Engels et al., *Angew. Chem. Int. Ed. Engl.*, 28:716–734 [1989]). These methods include inter alia, the phosphotriester, phosphoramidite, and H-phosphonate methods of nucleic acid synthesis. Typically, the native genomic DNA will be several hundred base pairs in length. Since the chemical synthesis methods set forth herein can be used to make nucleic acid sequences of up to about 100 base pairs, the native genomic DNA can be synthesized in 100 bp fragments which can then be ligated together using standard DNA ligation methods.

The native genomic DNA or cDNA molecule must be generated in sufficient quantity for genetic manipulation and insertion into ES cells. Amplification may be conducted by 1) placing the sequence into a suitable vector and transforming bacterial or other cells that can rapidly amplify the vector, 2) by PCR amplification, 3) by synthesis with a DNA synthesizer, or 4) by other suitable methods.

2. Preparation of a Knockout Construct

The native genomic DNA or cDNA molecule to be used in making the knockout construct can be digested with one or more restriction enzymes selected to cut at a location(s) such that a second DNA molecule encoding a marker gene can be inserted in the proper position within the native genomic DNA or cDNA molecule. The proper position for marker gene insertion is one that will serve to decrease or prevent expression of the native gene; this position will depend on various factors such as the restriction sites in the sequence to be cut, and whether an exon sequence or a promoter sequence, or both is (are) to be interrupted (i.e., the precise location of insertion necessary to inhibit promoter function or to inhibit expression of the native exon). Preferably, the enzyme(s) selected for cutting the native genomic DNA or cDNA molecule will generate a longer arm and a shorter arm, where the shorter arm is at least about 300 base pairs (bp). In some cases, it will be desirable to actually delete a portion or even all of one or more introns or exons of this native genomic or cDNA molecule so as to keep the length of the knockout construct comparable to the length of the endogenous genomic sequence after the marker gene has been inserted in the knockout construct. In these cases, the native genomic DNA or cDNA molecule can be cut with appropriate restriction endonucleases such that a fragment of the proper size can be removed.

The marker gene used in the knockout construct can be any nucleic acid molecule that is detectable and/or assayable after it has been incorporated into the genomic DNA of the mammal, however typically it is an antibiotic resistance gene or other gene whose expression or presence in the genome can easily be detected. Preferably, the marker gene encodes a polypeptide that does not naturally occur in the mammal. The marker gene is usually operably linked to its own promoter or to another strong promoter from any source that will be active or can easily be activated in the cell into which it is inserted; however, the marker gene need not have its own promoter attached, as it may be transcribed using the promoter of the gene to be knocked out. In addition, the marker gene will normally have a polyA sequence attached to its 3' end; this sequence serves to terminate transcription of the gene. Preferred marker genes are any antibiotic resistance gene such as neo (the neomycin resistance gene) and beta-gal (beta-galactosidase).

After the native genomic DNA or cDNA molecule has been digested with the appropriate restriction enzyme(s), the marker gene molecule can be ligated with the native genomic DNA or cDNA molecule using methods well known to the skilled artisan and described in Sambrook et al., supra. The ends of the DNA molecules to be ligated must be compatible; this can be achieved by either cutting all fragments with those enzymes that generate compatible ends, or by blunting the ends prior to ligation. Blunting is done using methods well known in the art, such as for example by the use of Klenow fragment (DNA polymerase I) to fill in sticky ends.

The ligated DNA knockout construct may be transfected directly into embryonic stem cells (discussed below), or it may first be placed into a suitable vector for amplification prior to insertion. Preferred vectors are those that are rapidly amplified in bacterial cells such as the pBluescript II SK vector (Stratagene, San Diego, Calif.) or pGEM7 (Promega Corp., Madison, Wis.).

3. Transfection of Embryonic Stem Cells

This invention contemplates production of a knockout mammal from any species of rodent, including without limitation, rats, hamsters, and mice. Preferred rodents include members of the Muridae family, including rats and mice. Generally, the embryonic stem cells (ES cells) used to produce the knockout mammal will be of the same species as the knockout mammal to be generated. Thus for example, mouse embryonic stem cells will usually be used for generation of knockout mice.

Embryonic stem cells are typically selected for their ability to integrate into and become part of the germ line of a developing embryo so as to create germ line transmission of the knockout construct. Thus, any ES cell line that is believed to have this capability is suitable for use herein. One mouse strain that is typically used for production of ES cells, is the 129J strain. A preferred ES cell line is murine cell line D3 (American Type Culture Collection, 12301 Parklawn Drive, Rockville, Md. 20852-1776 USA, catalog no. CRL 1934). The cells are cultured and prepared for DNA insertion using methods well known to the skilled artisan such as those set forth by Robertson (in: *Teratocarcinomas and Embryonic Stem Cells: A Practical Approach*, E. J. Robertson, ed. IRL Press, Washington, D.C. [1987]), by Bradley et al. (*Current Topics in Devel. Biol.*, 20: 357–371 [1986]) and by Hogan et al. (*Manipulating the Mouse Embryo: A Laboratory Manual*, Cold Spring Harbor Laboratory Press, Cold Spring Harbor, N.Y. [1986]).

Insertion of the knockout construct into the ES cells can be accomplished using a variety of methods well known in the art including for example, electroporation, microinjection, and calcium phosphate treatment (see Lovell-Badge, in Robertson, ed., supra). A preferred method of insertion is electroporation.

Each knockout construct DNA molecule to be inserted into the cell must first be linearized if the knockout construct has been inserted into a vector. Linearization is accomplished by digesting the DNA with a suitable restriction endonuclease selected to cut only within the vector sequence and not within the knockout construct sequence.

For insertion of the DNA sequence, the knockout construct DNA is added to the ES cells under appropriate conditions for the insertion method chosen. Where more than one construct is to be introduced into the ES cell, the DNA molecule encoding each construct can be introduced simultaneously or sequentially.

If the ES cells are to be electroporated, the ES cells and knockout construct DNA are exposed to an electric pulse using an electroporation machine and following the manufacturer's guidelines for use. After electroporation, the cells are typically allowed to recover under suitable incubation conditions. The cells are then screened for the presence of the knockout construct.

Screening can be accomplished using a variety of methods. Where the marker gene is an antibiotic resistance gene, the cells can be cultured in the presence of an otherwise lethal concentration of antibiotic. Those cells that survive have presumably integrated the knockout construct. If the marker gene is other than an antibiotic resistance gene, a Southern blot of the ES cell genomic DNA can be probed with a sequence of DNA designed to hybridize only to the marker sequence. Finally, if the marker gene is a gene that encodes an enzyme whose activity can be detected (e.g., beta-galactosidase), the enzyme substrate can be added to the cells under suitable conditions, and the enzymatic activity of the marker gene can be analyzed.

The knockout construct may integrate into several locations in the ES cell genome, and may integrate into a different location in each cell's genome, due to the occurrence of random insertion events; the desired location of insertion is in a complementary position to the native, endogenous gene to be knocked out. Typically, less than about 1–5 percent of the ES cells that take up the knockout construct will actually integrate the knockout construct in the desired location. To identify those cells with proper integration of the knockout construct, chromosomal DNA can be extracted from the cells using standard methods such as those described by Sambrook et al., supra. This DNA can then be probed on a Southern blot with a probe or probes designed to hybridize to the knockout construct DNA digested with (a) particular restriction enzyme(s). Alternatively, or additionally, a specific genomic DNA sequence can be amplified by PCR with probes specifically designed to amplify that DNA sequence such that only those cells containing the knockout construct in the proper position will generate DNA fragments of the proper size.

4. ES Cell Incorporation/Implantation of Embryos

After suitable ES cells containing the knockout construct in the proper location have been identified, the cells are incorporated into an embryo. Incorporation may be accomplished in a variety of ways.

A preferred method of incorporation of ES cells is by microinjection into an embryo that is at the blastocyst stage of development. For microinjection, about 10–30 cells are collected into a micropiper and injected into a blastocyst to integrate the ES cell into the developing blastocyst.

The suitable stage of development for the blastocyst is very species dependent, however for mice it is about 3.5 days. The blastocysts can be obtained by perfusing the uterus of pregnant females. Suitable methods for accomplishing this are known to the skilled artisan, and are set forth for example by Bradley (in Robertson, ed., supra).

While any blastocyst of the right age/stage of development is suitable for use, preferred blastocysts are male and have genes coding for a coat color or other phenotypic marker that is different from the coat color or other phenotypic marker encoded by the ES cell genes. In this way, the offspring can be screened easily for the presence of the knockout construct by looking for mosaic coat color or other phenotypic marker (indicating that the ES cell was incorporated into the developing embryo). Thus, for example, if the ES cell line carries the genes for white fur, the embryo selected will preferably carry genes for black or brown fur.

An alternate method of preparing an embryo containing ES cells that possess the knockout construct is to generate "aggregation chimeras". A morula of the proper developmental stage (about 2½ days old for mice) is isolated. The zona pellucida can be removed by treating the morula with a solution of mild acid for about 30 seconds, thereby exposing the "clump" of cells that comprise the morula. Certain types of ES cells such as the R1 cell line for mice can then be co-cultured with the morula cells, forming an aggregation chimera embryo of morula and ES cells.

A refinement of the aggregation chimera embryo method can be used to generate an embryo comprised of essentially only the ES cells containing the knockout construct. In this technique, a very early stage zygote (e.g., a two-cell stage zygote for mice) is given a mild electric shock. This shock serves to fuse the nuclei of the cells in the zygote thereby generating a single nucleus that has two-fold (or more) the DNA of a naturally occurring zygote of the same developmental stage. These zygotic cells are excluded from the developing embryo proper, and contribute only to forming accessory embryonic structures such as the extra-embryonic membrane. Therefore, when ES cells are co-cultured with the zygotic cells, the developing embryo is comprised exclusively of ES cells.

After the ES cells have been incorporated, the aggregation chimera can be implanted into the uterus of a pseudopregnant foster mother. While any foster mother may be used, they are typically selected for their ability to breed and reproduce well, and for their ability to care for their young. Such foster mothers are typically prepared by mating with vasectomized males of the same species. The pseudopregnant stage of the foster mother is important for successful implantation, and it is species dependent. For mice, this stage is about 2–3 days pseudopregnant.

5. Screening for the Presence of the Knockout Gene

Offspring that are born to the foster mother may be screened initially for mosaic coat color or other phenotype marker where the phenotype selection strategy (such as coat color, as described above) has been employed. In addition, or as an alternative, chromosomal DNA obtained from tail tissue of the offspring may be screened for the presence of the knockout construct using Southern blots and/or PCR as described above. Offspring that appear to be mosaics can then be crossed to each other if they are believed to carry the knockout construct in their germ line; such crosses may generate homozygous knockout animals. If it is unclear whether the offspring will have germ line transmission, they can be crossed with a parental or other strain and the offspring screened for heterozygosity. The heterozygotes are identified by Southern blots and/or PCR amplification of the DNA, as set forth above. These heterozygotes can then be crossed with each other to generate homozygous knockout offspring. Homozygotes may be identified by Southern blotting of equivalent amounts of genomic DNA from mammals that are the product of this cross, as well as mammals of the same species that are known heterozygotes, and wild-type mammals. Probes to screen the Southern blots for the presence of the knockout construct in the genomic DNA can be designed as set forth above.

Other means of identifying and characterizing the knockout offspring are available. For example, Northern blots can be used to probe mRNA obtained from various tissues of the offspring for the presence or absence of transcripts encoding either the gene knocked out, the marker gene, or both. In addition, Western blots can be used to assess the level of expression of the gene knocked out in various tissues of these offspring by probing the Western blot with an antibody against the protein encoded by the gene knocked out, or an antibody against the marker gene product, where this gene is expressed. Finally, in situ analysis (such as fixing the cells and labeling with antibody) and/or FACS (fluorescence activated cell sorting) analysis of various cells from the offspring can be conducted using suitable antibodies to look for the presence or absence of the knockout construct gene product.

Uses of Knockout Mammal

The mammal of this invention will have a variety of uses depending on the gene or genes that have been suppressed. Where the gene or genes suppressed encode proteins believed to be involved in immune system function (as is the case for IL-2R$\alpha$, $\beta$ and $\gamma$ chains), such as inflammation, autoimmunity, or immunosuppression, the mammal may be used to screen for drugs useful for immunomodulation, i.e., drugs that either enhance or inhibit these activities. Screening for useful drugs typically involves administering the candidate drug over a range of doses to the mammal, and assaying at various time points for the immunomodulatory effect(s) of the drug on the immune disorder being evaluated. Such assays would include, for example, looking for increased or decreased T and B cell levels, increased or decreased immunoglobulin production, increased or decreased levels and/or activity of chemical messengers such as interleukins, and/or increased or decreased levels of expression of a particular gene(s) involved in the immune response.

For example, patients undergoing chemotherapy often experience immunosuppression. It would be desirable to activate the immune system of such individuals by administering to the patient a therapeutic agent capable of producing such an effect. A mammal of the present invention could be used to screen a variety of compounds, either alone or in combination, to determine whether partial or total restoration or activation of the immune response results from the use of such drug.

The same strategy could be applied to find compounds that would be useful in suppressing the inflammatory response observed in many patients with arthritis, or compounds that would be useful in suppressing the autoimmune phenomenon observed in patients with rheumatoid arthritis and lupus.

In addition, a mammal of the present invention can be useful for evaluating the development and function of various components of the immune system, and for studying the effects of particular gene mutations. For example, in a mammal not expressing one chain of the IL-2R, one can analyze the effect of the lack of such expression on other compounds of the immune system such as IL-2 and other interleukins. Since it is believed that IL-2Rβ is responsible for signal transduction in response to IL-2 binding to IL-2R, one can analyze the effects of a lack of signal transduction by IL-2 when IL-2Rβ is knocked out. In addition, since IL-2Rβ is a component of the IL-15 receptor complex, one can analyze the effects of IL-15 and IL-15 receptor activity on other components of the immune system when IL-2Rβ is knocked out. Similarly, IL-2Rγ is a component of both the IL-4 and IL-7 receptors; thus, one can analyze the effect of the lack of expression of this protein on other components of the immune system in an effort to better understand the interplay and relationship of various immune system components.

Other uses will be readily apparent to one of skill in the art.

The invention will be more fully understood by reference to the following examples. These examples are not to be construed in any way as limiting the scope of this invention.

EXAMPLES

Example I: Preparation of a an IL-2 Rβ Knockout Mouse

1. Preparation of Knockout DNA Construct

A genomic clone of the murine IL-2 receptor β chain ("IL-2Rβ") was isolated from a mouse BALB/c genomic DNA library (Miyatake et al., *Proc. Natl. Acad. Sci. USA*, 82:316–320 [1985]) using the mouse cDNA clone λMIL2Rβ-26 (Kono et al., *Proc. Natl. Acad. Sci. USA*, 87: 1806–1810 [1990]) as a probe. The genomic IL-2Rβ DNA molecule was digested with restriction enzymes BglII and NdeI, and an approximately 2.4 kb fragment containing exon 6 and a portion of exon 7 was isolated using standard agarose gel electrophoresis procedures. This fragment was then ligated into the vector pBluescript II (Stratagene Corp., LaJolla, Calif.) previously digested with BamHI and EcoRI. An approximately 1.1 kb (XhoI-SalI fragment obtained from the construct pMCIneoPolA (Thomas et al., *Cell*, 51:503–512 [1987]) was inserted into the IL-2Rβ/pBluescript II construct by first digesting this construct with the restriction enzyme AatII; this enzyme cut the IL2Rβ fragment in the exon 6 coding region. The resulting construct containing the IL2Rβ exon 6 (disrupted with the neogene insert) and a part of exon 7 in the pBluescript II vector was named pIL-2β neoSens. The neo gene and the IL-2Rβ gene were transcribed in the same direction. pIL-2βneoSens was transfected into the *E. coli* bacteria strain DH5-α for amplification and was then purified from the cells using the standard alkaline lysis/CsCl techniques.

2. Electroporation and Injection of Embryonic Stem Cells

The purified plasmid knockout construct was linearized by digestion with restriction endonuclease HindIII thereby generating a shorter arm and a longer arm of IL-2Rβ DNA fragments on either side of the neo gene. This knockout construct is depicted in FIG. 1. The linearized knockout construct was then transfected into the embryonic stem cell line D3 as follows: about 5 pmol of linearized DNA was added to about $5 \times 10^6$ ES cells in a volume of about 800 µl of culture media. The cells were pulsed at about 0.34 kilovolts and about 250 µF, and each vial of cells was then plated on to two 10 cm cell culture plates. The plates were precoated with 1 percent gelatin, and contained about 10 ml of DMEM medium (Gibco/BRL, Grand Island, N.Y.), 15 percent fetal calf serum (Gibco/BRL, Grand Island, N.Y. or equivalent from Hyclone Labs, Logan, Utah), and leukemia inhibitory factor (Fung-Leung et al. *Cell*, 65:443–449 [1991]), $10^{-4}$ M B-mercaptoethanol, 2 mM L-glutamine, and 1 mM sodium pyruvate. After two days, neo selection was started by adding the antibiotic G418 at about 250 µg/ml to the cultures. Cells that survived in the presence of G418 most likely contained the knockout construct. These cells were then screened to verify that the cells that had incorporated the knockout construct in the genomic DNA. Screening was accomplished using the polymerase chain reaction (PCR) method for DNA amplification. Two primers were used in PCR. The first primer was directed to a sequence specific for a portion of exon 7 of IL-2Rβ and is set forth below; the second primer, also set forth below, hybridizes to a region about 20–40 base pairs upstream of the polyA signal sequence in pMC1neo PolA.

Primer 1 (SEQ ID NO:1):

TGGCCTTGTCCGAAAGGTCA

Primer 2 (SEQ ID NO:2):

CTTGACGAGTTCTTCTGAGG

Southern blots of genomic DNA from control and transfected cells were analyzed to identify those transfected cells containing the knockout construct in the proper location and orientation of the chromosomal DNA, (i.e., to identify those cells that had undergone homologous recombination). The Southern blots were probed with two probes. The first probe was about 300 base pairs (bp), and hybridized to a portion of exon 7 located 3' of the NdeI site and 5' of the EcoRI site in exon 7. The second probe was a fragment of the neo gene and was generated by digesting the plasmid pMC1NeoPolA (described above) with HindIII and XhoI, and isolating the 1.2 kb fragment using standard agarose gel electrophoresis procedures.

Cell lines containing the IL-2Rβ-neo insert that had integrated properly into the genomic DNA were prepared for micro-injection into murine embryos by trypsin treatment following methods described by Robertson (*Teratocarcinomas and Embryonic Stem Cells: A Practical Approach*, IRL Press, Washington, D.C., [1987], Robertson, E. J., ed). The mouse embryos injected were 3.5 day old blastocysts obtained by perfusing the uterus of female C57BL/6 mice that had been mated with male mice. About 15–30 ES cells were injected into each blastocyst. After injection of the embryonic stem cells into the blastocysts, the blastocysts were implanted into CD1 pseudopregnant female mice at day 2.5 postcoitum for gestation. The chimeric male offspring were identified by agouti coat color and were crossed with female C57BL/6 mice. Germline transmission of the knockout construct was determined by coat color of the $F_1$ pups; agouti pups were identified as knockouts. $F_1$ heterozygous pups were crossed with each other to generate $F_2$ homozygotes. The homozygotes were identified by PCR amplification. The primers used for this PCR analysis were Primer 1, as set forth above, and:

Primer 3 (SEQ ID NO:3)

CCAGGTCTCTCACTACATTG

DNA obtained from tail tissue was used as the PCR template. PCR conditions were 30 cycles of 94° C. for 30 sec., 60° C. for 60 sec., and 72° C. for 90 sec.

An approximately 800 bp band was amplified in the DNA of wild-type and heterozygous IL-2Rβ mice, while this band was undetectable in the homozygous knockout mice.

3. Screening Mice for Knockout Construct

The offspring of these matings were evaluated for the presence of the knockout construct using PCR. Two combinations of primers were used in the PCR analysis. First, primers 1 and 2 (set forth above) were used to distinguish between wild type (which gave a negative response to PCR) and heterozygous and homozygous (which both gave positive responses to PCR). Next, primers 1 and 3 were used for PCR analysis to distinguish between heterozygous knockout mice (a positive PCR response) and homozygous knockout mice (a negative PCR response).

4. Analysis of Effects of Knockout Gene

A. T Cell Development

The development of T cells in IL2-Rβ knockout mice was analyzed by examining thymocytes from these mice at various ages. Thymocytes were obtained as follows. The mice were sacrificed and the thymus was removed. The thymus was gently crushed and then passed through a fine mesh screen to obtain a suspension of single thymocytes in phosphate buffered saline (PBS).

The thymocyte phenotype from wild-type, heterozygous, and homozygous IL2-Rβ mice was analyzed by fluorescence activated cell sorting (FACScan) of the thymocytes after labeling with rat anti-mouse CD4 and rat anti-mouse CD8α monoclonal antibodies. The anti-CD4 antibody was labeled with phycoerythrin (PE); the anti-CD8α antibody was labeled with fluorescein diisothiocyanate (FITC). Both antibodies were obtained from Pharmingen (San Diego, Calif.). About 3 μl of antibody was added to about $10^6$ cells in a total volume of about 100 μl. Incubation conditions were about 20–30 minutes on ice. After incubation the cells were placed into 5 ml tubes and washed with PBS containing 0.1% $NaN_3$ and 1% bovine serum albumin (BSA).

The thymocytes from 8 and 21 day old wild-type, heterozygous knockout and homozygous knockout mice were comparable in their cell surface phenotypes. However, 6 week old homozygous mice had a reduced number of thymocytes (about $1.6 \times 10^7 \pm 0.5$ [n=3] as compared to wild-type and heterozygous knockout mice (about $11.4 \times 10^7 \pm 1.5$ [n=4].

B. Hematocrit and Reticulocyte Counts

The hematocrits of IL-2Rβ wild-type and homozygous knockout mice were measured regularly by centrifuging peripheral blood obtained from each mouse for 5 minutes in heparin coated capillary tubes and determining the ratio of cell volume to total blood volume. The results are shown in Table I. The hematocrit values are shown as a percentage of total blood volume. As is apparent, mild anemia was observed in 3 week old homozygous knockout mice (–/–) as compared to the heterozygous knockout mice (+/–); this anemia became more pronounced in older mice.

Reticulocyte counts were assessed by staining peripheral blood samples with new methylene blue and counting the number of reticulocytes per 1,000 red blood cells.

| Mice | Age | | | | | |
| | 3 WEEK | | 5 WEEK | | 7 WEEK | |
| IL-2Rβ | Ht | Ret | Ht | Ret | Ht | Ret |
| --- | --- | --- | --- | --- | --- | --- |
| +/–#1 | 48 | 52 | 54 | 31 | 52 | 63 |
| +/–#2 | 43 | 52 | 50 | 12 | 46 | 44 |
| –/–#1 | 33 | 164 | 29 | 86 | 9 | 4 |
| –/–#2 | 33 | 137 | 25 | 2 | 18 | 1 |

Age refers to the age of the mice examined.
Two +/– and two –/– mice were examined periodically.
"Ht" refers to hematocrit; "Ret" refers to reticulocyte counts per 1000 red blood cells.

C. T Cell Response to Mitogens

T cells were isolated from mesenteric and inguinal lymph nodes of IL-2Rβ wild-type, heterozygous, and homozygous knockout mice as follows. The lymph nodes were obtained from sacrificed mice and passed through a fine mesh screen using a rubber tipped rod. Red blood cells were lysed using Gay's lysis solution. Individual cells were collected into either Iscove's medium or PBS. This cell suspension was then passed over a T cell Enrichment Column (R&D Systems catalog no. MTCC-1000, Minneapolis, Minn.) following the manufacturer's instructions for obtaining the purified T cells. About $1 \times 10^5$ T cells were placed into each well of a 96 well flat-bottom microtiter plate along with about $5 \times 10^5$ irradiated (2000 rads) splenic feeder cells (which serve as antigen presenting cells). RPMI-1640 medium (Gibco/BRL, Gaithersburg, Md.) supplemented with about 10% fetal calf serum, and about $10^{-4}$ M β-mercaptoethanol was added to each well. Various stimulatory factors were then added including either:

1) rabbit anti-hamster IgG (about 10 μg/ml) incubated at about 4° C. overnight followed by about 50 μl of 10 μg/ml hamster anti-CD3 monoclonal antibody for about 3 hours at 37° C. (both antibodies were obtained from Pharmingen, San Diego, Calif.);

2) rabbit anti-hamster IgG (about 10 ug/ml) incubated at about 4° C. overnight followed by about 50 μl of 10 μg/ml hamster anti TCRαβ monoclonal antibody (both obtained from Pharmingen, San Diego, Calif.);

3) rabbit anti-hamster IgG only;

4) About 2.5 μg/ml staphylococcal enterotoxin B (SEB; Sigma Chemical Company, St. Louis, Miss., catalog no. S-4881);

5) Interleukin-2 at a concentration of about 100 U/ml (Genzyme Inc., Cambridge Mass., catalog no. MIL-2);

6) PMA (Sigma Chemical Company, St. Louis, Miss.) at about 12.5 ng/ml plus calcium ionophore (A23187) at about 125 ng/ml;

7) PMA plus IL-2, both at the concentrations listed above; or 8) concanavalin A (Sigma Chemical Company, St. Louis, Miss.) at about 2.5 μg/ml.

The final volume of each well including cells, medium, and stimulatory factor(s) was about 200 μl.

After 3 days the cells were pulsed for about ten hours with about 1 μCi of [$^3$H]-thymidine, and the amount of radioactivity in the cells was measured.

Figure 2A:
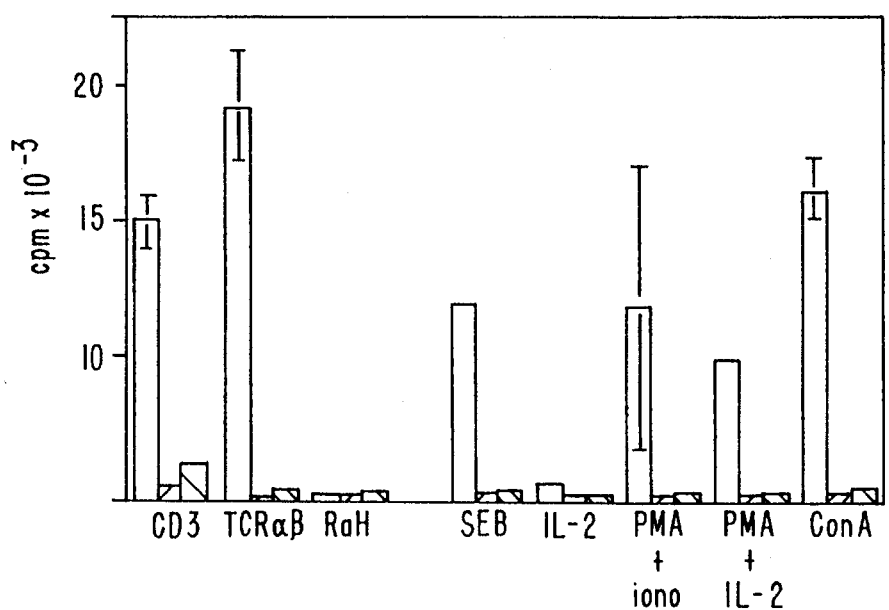
FIGS. 2A and 2B depict the response of murine T cells to various stimulatory agents.
Figure 2B:
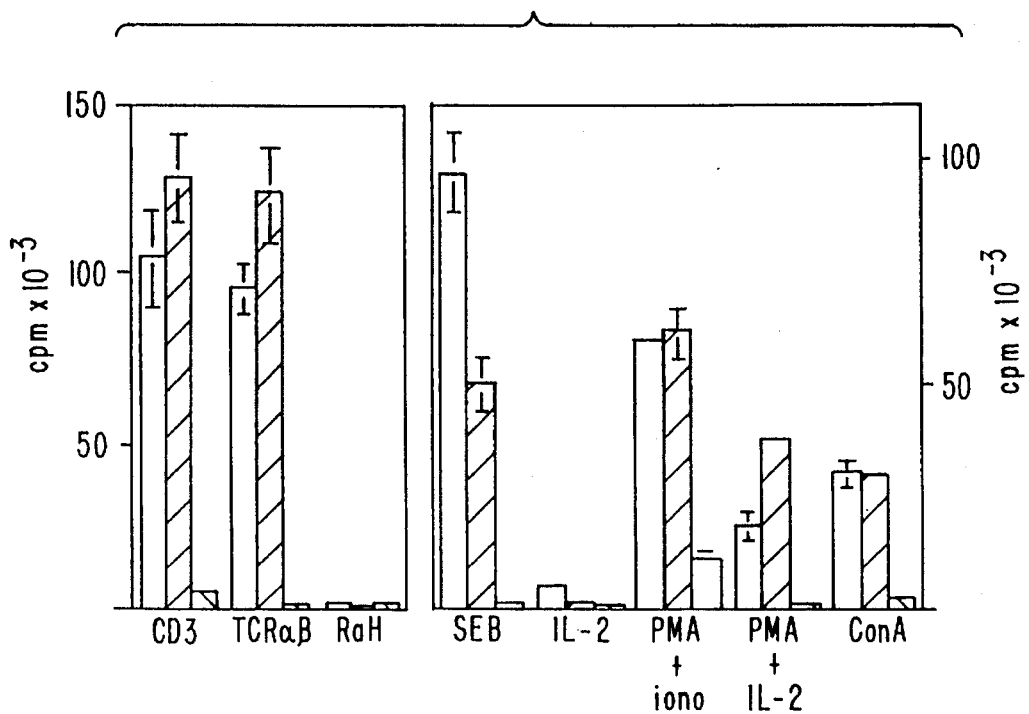

The results are shown in FIG. 2. As can be seen, the T cells from homozygous IL-2Rβ knockout mice did not proliferate significantly in response to IL-2, or to polyclonal T cells activators such as concanavalin A, SEB, or PMA plus calcium ionophore as compared to wild-type and heterozygous IL-2Rβ knockout mice. In addition, the T cells from homozygous IL-2Rβ knockout mice were not significantly responsive to crosslinking of the TCR with antibodies against CD3 or TCRαβ as compared to T cells from wild-type and heterozygous IL-2Rβ knockout mice.

D. CTL Response

Figure 3A:
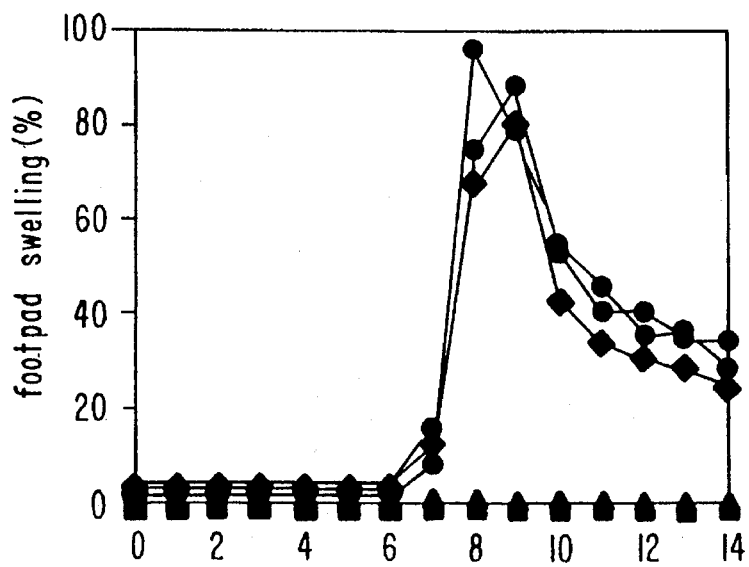
Figure 3B:
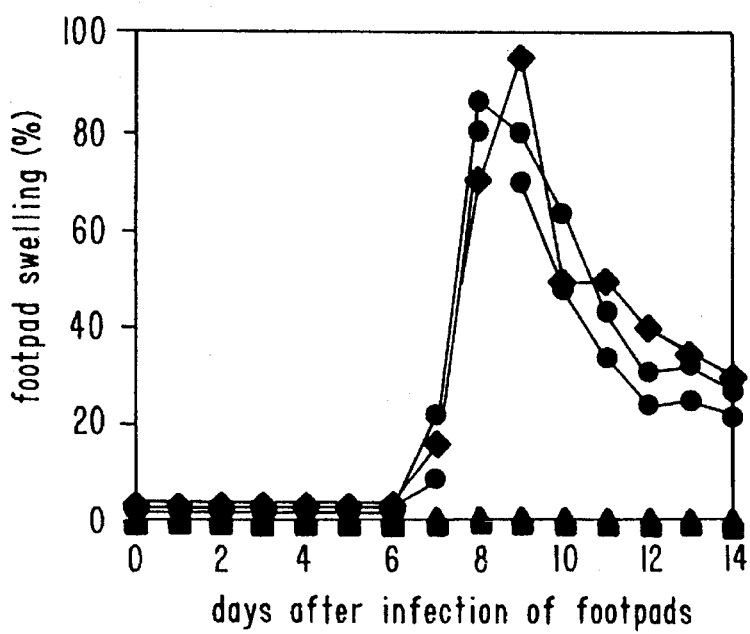
FIG. 3B shows the response of T cells from 6 week old mice. Open boxes represent the response of T cells from wild type mice; gray colored boxes represent the response of T cells from heterozygous knockout mice; and solid black boxes represent the response of T cells from homozygous knockout mice. For both FIG. 3A and 3B, the stimulants added are as indicated.

The cytotoxic lymphocyte responses (CTL) of wild-type, heterozygous, and homozygous IL-2Rβ knockout mice were evaluated using the lymphocytic choriomeningitis virus (LCMV). The mice were injected with about 2000 pfu LCMV (Buchmeier et al., *Adv. Immunol.*, 30:275–312 [1980]) on day 0. The results are shown in FIG. 3. Neither the $CD_{8+}$ mediated swelling response (which is typically observed at about day 8) nor the $CD_{4+}$ mediated swelling response (which usually occurs at about day 10) was observed in the homozygous knockout mice; these responses were apparent in the wild-type and heterozygous knockout mice.

E. B Cell Response

The B cell response to vesicular stomatitis virus (VSV) was evaluated in the heterozygous, and homozygous IL-2Rβ knockout mice. The tail vein of the mice was injected with either about $2\times10^5$ pfu or $2\times10^6$ pfu of VSV (New Jersey serotype). Neutralizing antibody titers were determined by drawing blood from the retroorbital venus plexus on days 4, 6, 8 and 12 after infection. The serum was separated using the microtainer system purchased from Becton-Dickinson Company (Mountain View, Calif.). Data on neutralizing antibodies against VSV was calculated as described by Roost et al. (*Eur. J. Immunol.*, 18:511–518 [1988]). This calculation essentially involved heat inactivating the sera at about 56° C. for 30 minutes and then diluting the sera about 40 fold. Serial dilutions of 1 in 2 were then prepared in 96-well plates. Each dilution was incubated with about 200 pfu of VSV for about 90 minutes, after which time the serum-VSV mixtures were transferred to vero cell monolayers in 96 well plates. After about 60 minutes, the cultures were overlayed with methylcellulose (final concentration about 0.5%). After about 24 hours, VSV plaques were visible by staining the vero cells with crystal violet prepared in formaldehyde and alcohol. The serum dilution that reduced the number of plaques by more than 50% was taken as the titer. IgG titers were determined by first treating the serum samples with β-mercaptoethanol (0.1M; 60 minutes at room temperature) before diluting 40-fold.

Figure 4A:
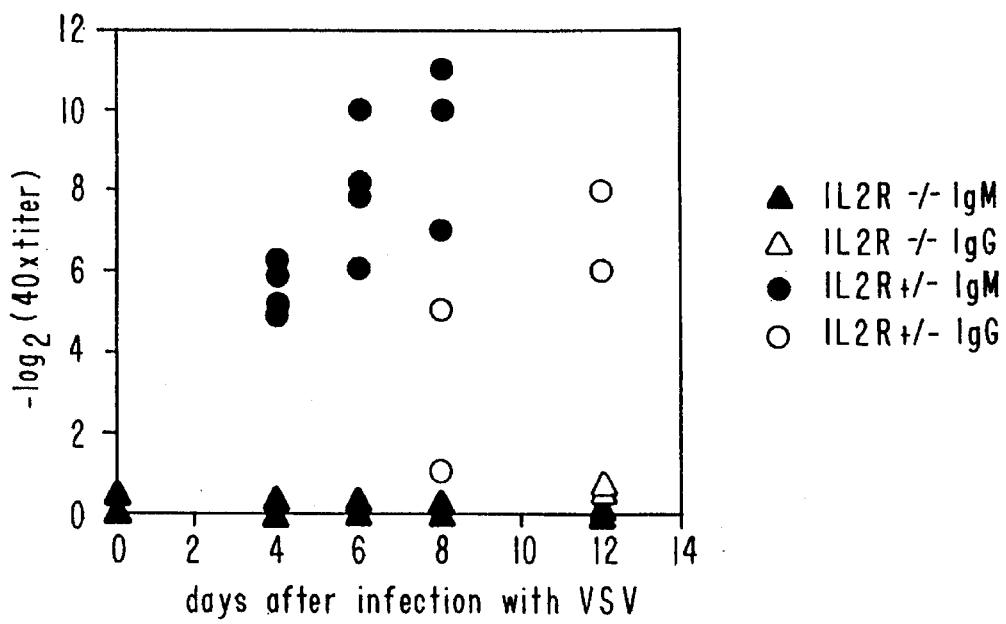
FIG. 4A shows antibody titers when $2 \times 10^6$ pfu of VSV was injected.
Figure 4B:
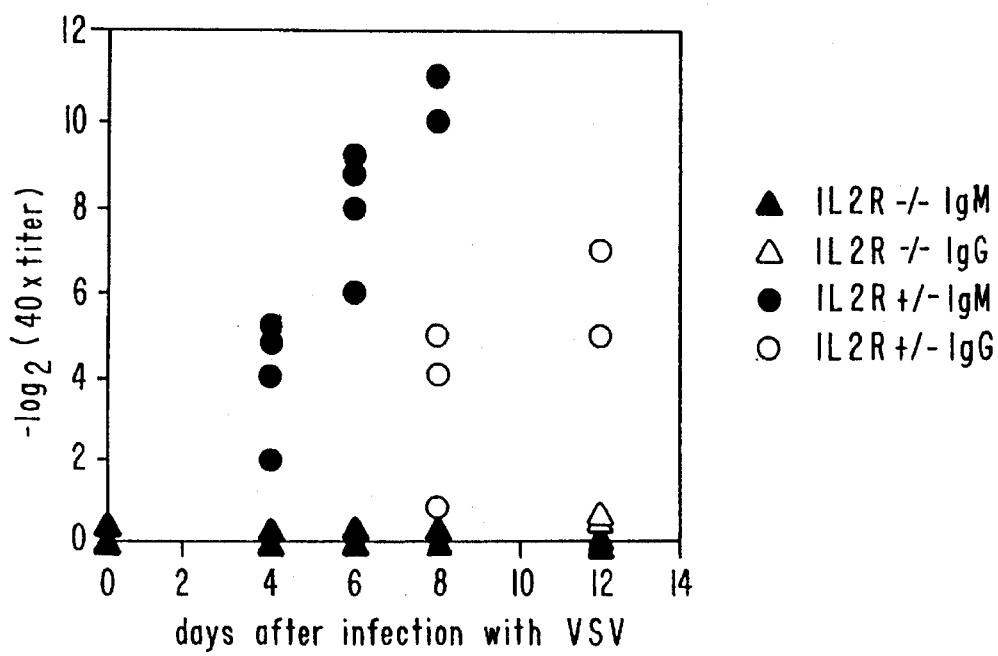
FIG. 4B shows antibody titers when $2 \times 10^5$ pfu of VSV was injected.

The results are shown in FIG. 4. The homozygous knockout mice were unable to mount detectable levels of IgM or IgG in response to viral infection. Heterozygous knockout mice however, did mount high levels of both IgM and IgG in response to viral infections.

F. Determination of Immunoglobulin Isotypes

The level of immunoglobulin isotypes in the sera of wild type, heterozygous IL-2Rβ knockout and homozygous IL-2Rβ knockout mice was determined at ages 3, 5 and 8 weeks. Sera were obtained as described above in Section E. Isotype quantitation was evaluated using a panel of mouse isotype-specific antibodies purchased from Southern Biotechnology Associates Inc. (Birmingham, Ala.) and following the manufacturer's protocol. Graphs were prepared from the OD of sequentially diluted standard immunoglobulins of each isotype; the isotype levels of each sample were then determined from the standard graphs.

Figure 5:
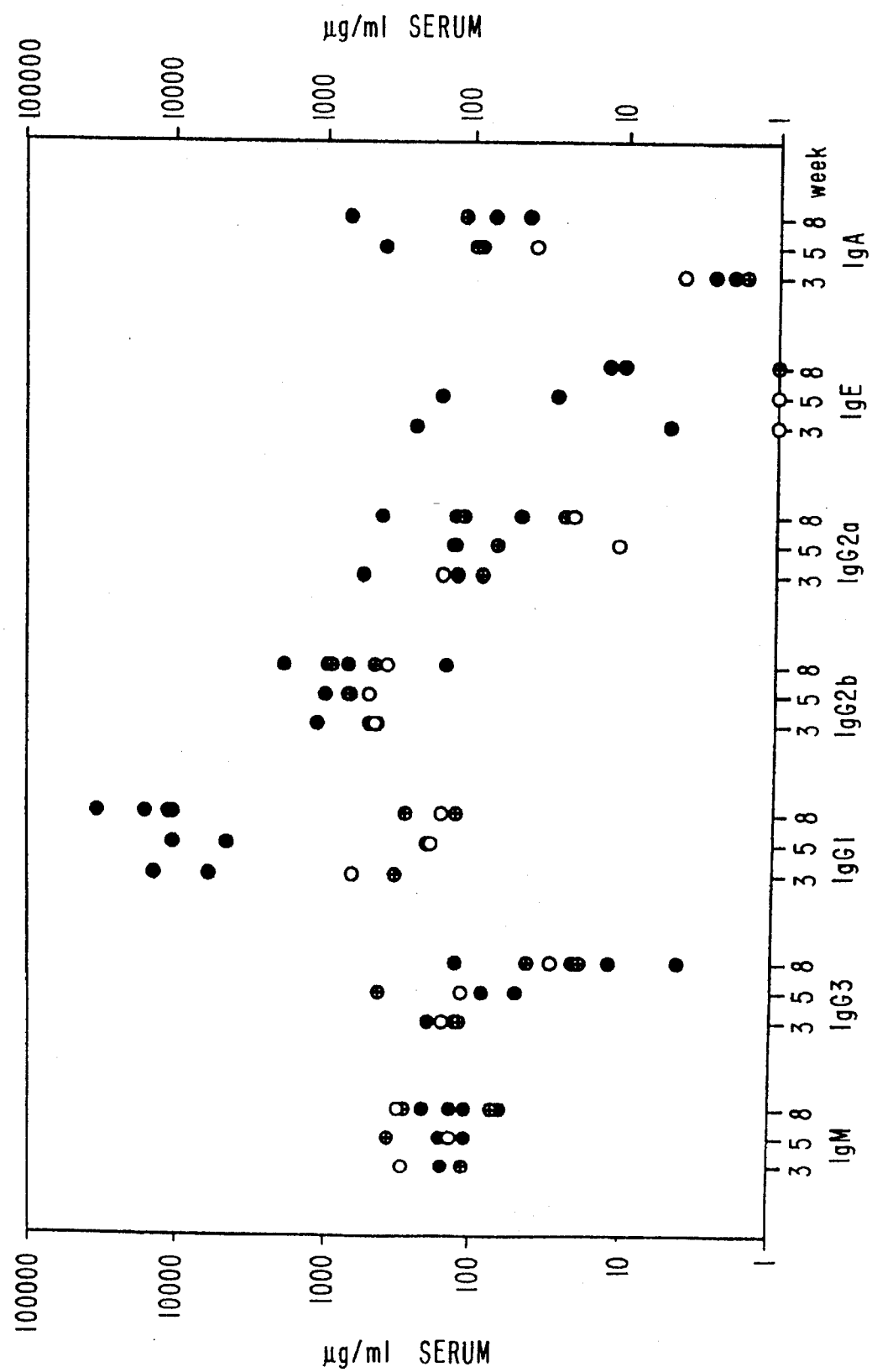
FIG. 5 depicts the level of antibody isotypes in wild-type (open circles), heterozygous IL-2Rβ knockout (hatched circles) and homozygous IL-2Rβ knockout (dark circles) mice. The antibody classes are indicated. The numbers "3, 5 and 8" on the X axis refer to the age of the mice in weeks when tested for each isotype.

The results are presented in FIG. 5. As can be seen, IgG1 and IgE were significantly elevated in the homozygous knockout mice as compared to the heterozygous and wild-type mice.

Since the level of IgE antibodies was elevated in the homozygous knockout mice, the possibility of spontaneous autoimmunity in these mice was analyzed by evaluating the level of anti-nuclear and anti-DNA antibodies in the sera of the mice. Anti-nuclear antibody and anti-native DNA antibody detection kits were purchased from Sigma Diagnostics (St. Louis, Miss.) and were used according to the manufacturer's protocol except that FITC-conjugated anti-mouse antibody was used in place of FITC-conjugated anti-human Ig antibody. The sera from the mice were diluted either 10, 20, 40 or 80 fold as indicated in Table 2.

TABLE 2

| Age (weeks) | IL-2Rβ Genotype[c] | Autoantibody (serum dilution) | |
|---|---|---|---|
| | | Antinuclear[a] | AntiDNA[a] |
| 3 | +/+ | −(×10) | −(×10) |
| 3 | +/− | −(×10) | −(×10) |
| 3 | −/− | +(×40) | ±b(×10) |
| 3 | −/− | +(×40) | +(×40) |
| 5 | +/+ | −(×10) | −(×10) |
| 5 | +/− | −(×10) | −(×10) |
| 5 | −/− | +(×80) | +(×80) |
| 5 | −/− | +(×80) | +(×80) |
| 8 | +/+ | −(×10) | −(×10) |
| 8 | +/− | −(×10) | −(×10) |
| 8 | +/− | −(×10) | −(×10) |
| 8 | −/− | +(×20) | −(×10) |
| 8 | −/− | +(×40) | +(×40) |
| 8 | −/− | +(×40) | +(×40) |

[a]Staining was judged at the indicated serum dilution; "−" refers to no detectable staining and "+" refers to detectable staining.
[b]Very weakly stained.
[c]Genotype: +/+ refers to wild-type;
+/− refers to heterozygous knockout; and
−/− refers to homozygous knockout The results are shown in Table 2. The homozygous knockout mice had elevated levels of both anti-nuclear antibodies and anti-DNA antibodies, since fluorescence staining was detected at greater serum dilutions (20, 40 or 80 fold) in these mice as compared to the wild-type and heterozygous knockout mice.

All literature cited herein is specifically incorporated by reference.

We claim:

1. A DNA construct comprising a mouse IL-2Rβ gene fragment spanning the region between the Bgl II site of intron 5 and the Nde I site at the 3' end of exon 7, wherein a neo gene cassette is inserted into the Aat II site of exon 6.

2. A mouse D3 embryonic stem cell line comprising the DNA construct of claim 1.

* * * * *

UNITED STATES PATENT AND TRADEMARK OFFICE
CERTIFICATE OF CORRECTION

PATENT NO. : 5,532,158

DATED : July 2, 1996

INVENTOR(S) : Haruhiko Suzuki, Tak W. Mak

Page 1 of 2

It is certified that error appears in the above-identified patent and that said Letters Patent is hereby corrected as shown below:

Column 2, line 47, insert --)-- after "[1990]".
Column 4, line 37, insert --,-- after "gene" (first occurrence).
Column 4, line 37, insert --,-- after "disruption" (second occurrence).
Column 5, line 45, change "IL-2β" to --IL-2γ--.
Column 6, line 11, change "IL-2 D" to --IL-2β--.
Column 9, line 20, change "micropiper" to --micropipet--.
Column 11, line 64, change "IL2Rβ" to --IL-2Rβ--.
Column 11, line 66, change "IL2Rβ" to --IL-2Rβ--.
Column 11, line 66, change "neogene" to --neo gene--.
Column 12, line 2, change "pIL-2βneoSens" to --pIL-2β neoSens--.
Column 12, line 27, delete "that" (second occurrence).
Column 13, line 30, change "IL2-Rβ" to --IL-2Rβ--.
Column 13, line 38, change "IL2-Rβ" to --IL-2Rβ--.
Column 13, line 54, insert --)-- after "[n=3]".
Column 13, line 56, insert --)-- after "[n=4]".

UNITED STATES PATENT AND TRADEMARK OFFICE
CERTIFICATE OF CORRECTION

PATENT NO. : 5,532,158
DATED : July 2, 1996
INVENTOR(S) : Haruhiko Suzuki, Tak W. Mak It is certified that error appears in the above-identified patent and that said Letters Patent is hereby corrected as shown below:

Column 13, line 65, change "Table I" to --Table 1--.
Column 14, line 6, insert --TABLE 1-- (centered).
Column 14, line 33, change "tads" to --rads--.
Column 14, line 44, change "ug/ml" to --µg/ml--.
Column 14, line 54, insert --,-- after "Cambridge".
Column 15, line 20, change "$CD_{8+}$" to --CD8+--.
Column 15, line 21, change "$CD_{4+}$" to --CD4+--.
TABLE 2, Column 16, line 35, change "±b(x10)" to --$±^{b}$(x10)--.

Signed and Sealed this

Seventeenth Day of February, 1998

*Attest:*

BRUCE LEHMAN

*Attesting Officer*   Commissioner of Patents and Trademarks